US008989844B2

(12) United States Patent
Cinquin et al.

(10) Patent No.: US 8,989,844 B2
(45) Date of Patent: Mar. 24, 2015

(54) IMAGING SYSTEM FOR FOLLOWING A SURGICAL TOOL IN AN OPERATION FIELD

(75) Inventors: Philippe Cinquin, St. Nazaire les Eymes (FR); Pierre Mozer, Vincennes (FR); Sandrine Voros, Sevres (FR); Jean-Alexandre Long, Bernin (FR); Josselin Duchateau, Grenoble (FR); Alexandre Moreau-Gaudry, Grenoble (FR); Clement Vidal, Grenoble (FR); Patrick Henri, Asnieres (FR)

(73) Assignees: Endocontrol, La Tronche (FR); Universite Joseph Fourier—Grenoble 1, Saint Martin d'Heres (FR)

( * ) Notice: Subject to any disclaimer, the term of this patent is extended or adjusted under 35 U.S.C. 154(b) by 482 days.

(21) Appl. No.: 12/674,832

(22) PCT Filed: Aug. 20, 2008

(86) PCT No.: PCT/EP2008/060867
§ 371 (c)(1),
(2), (4) Date: Jun. 4, 2010

(87) PCT Pub. No.: WO2009/027277
PCT Pub. Date: Mar. 5, 2009

(65) Prior Publication Data
US 2011/0130659 A1 Jun. 2, 2011

(30) Foreign Application Priority Data
Aug. 24, 2007 (FR) ...................................... 07 57158

(51) Int. Cl.
*A61B 5/00* (2006.01)
*A61B 19/00* (2006.01)

(52) U.S. Cl.
CPC ......... *A61B 19/52* (2013.01); *A61B 2019/5231* (2013.01); *A61B 2019/5278* (2013.01);
(Continued)

(58) Field of Classification Search
USPC .......... 600/407, 424–427, 462, 466, 109, 160
See application file for complete search history.

(56) References Cited

U.S. PATENT DOCUMENTS

| 5,197,476 | A | 3/1993 | Nowacki et al. |
| 5,494,041 | A | 2/1996 | Wilk |

(Continued)

FOREIGN PATENT DOCUMENTS

| EP | 1 561 420 A2 | 10/2005 |
| WO | 99/58065 A1 | 11/1999 |

(Continued)

OTHER PUBLICATIONS

Machine Translation of WO 2007/074201 A3 obtained Jun. 5, 2013.*
(Continued)

*Primary Examiner* — Ruth S Smith
(74) *Attorney, Agent, or Firm* — Miles & Stockbridge PC

(57) ABSTRACT

The invention concerns an imaging system to monitor at least one surgical instrument in an operative site inside a volume of the body of an animal, comprising: at least one endoscopic camera to obtain endoscopic data on the operative site, at least one ultrasound imaging device to obtain ultrasound data on the operative site, and a processing device to process the endoscopic and ultrasound data. The imaging system further comprising at least three markers intended to be positioned in the operative site, said markers being mobile relative to the instrument, each marker being adapted to be detected both by the endoscopic camera and by the ultrasound imaging device, so as to permit cross-mapping of the endoscopic and ultrasound data by the processing means.

25 Claims, 2 Drawing Sheets

(52) U.S. Cl.
CPC . *A61B2019/5289* (2013.01); *A61B 2019/5408* (2013.01); *A61B 2019/5425* (2013.01); *A61B 2019/5429* (2013.01); *A61B 2019/5437* (2013.01); *A61B 2019/5445* (2013.01); *A61B 2019/5495* (2013.01)
USPC ........... 600/427; 600/426; 600/462; 600/466; 600/473; 600/476; 600/109; 600/160

(56) References Cited

U.S. PATENT DOCUMENTS

| | | | | |
|---|---|---|---|---|
| 6,302,875 | B1 * | 10/2001 | Makower et al. | 604/528 |
| 6,419,680 | B1 * | 7/2002 | Cosman et al. | 606/130 |
| 6,694,168 | B2 * | 2/2004 | Traxel et al. | 600/426 |
| 7,652,259 | B2 * | 1/2010 | Kimchy et al. | 250/370.08 |
| 2001/0016684 | A1 | 8/2001 | Shahidi | |
| 2004/0152975 | A1 * | 8/2004 | Blevis | 600/427 |
| 2005/0261591 | A1 * | 11/2005 | Boctor et al. | 600/462 |
| 2006/0029525 | A1 * | 2/2006 | Laugharn et al. | 422/130 |
| 2006/0258933 | A1 * | 11/2006 | Ellis et al. | 600/407 |
| 2006/0262118 | A1 | 11/2006 | Barfuss et al. | |
| 2007/0029491 | A1 * | 2/2007 | Olden et al. | 250/370.08 |
| 2007/0078345 | A1 * | 4/2007 | Mo et al. | 600/459 |
| 2007/0157404 | A1 * | 7/2007 | Brewer et al. | 15/22.1 |
| 2008/0146897 | A1 * | 6/2008 | Alfano et al. | 600/310 |
| 2008/0221442 | A1 * | 9/2008 | Tolkowsky et al. | 600/425 |
| 2009/0203991 | A1 * | 8/2009 | Papaioannou et al. | 600/421 |

FOREIGN PATENT DOCUMENTS

| | | |
|---|---|---|
| WO | 2004/042546 A1 | 5/2004 |
| WO | 2006/008300 A1 | 1/2007 |
| WO | WO 2007074201 A3 * | 11/2007 |

OTHER PUBLICATIONS

International Search Report, PCT/EP2008/060867, Mar. 24, 2009 (6 pages).
A. Herline et. al; "Technical Advances Toward Interactive Image-Guided Laparoscopic Surgery"; Surgical Endoscopy, 2000; p. 675-679.
Peter Berkelman et. al; "Development and Testing of a Compact Endoscope Manipulator for Minimally Invasive Surgery"; (Journal of Computer Aided Surgery, 2005; vol. 10, No. 1, p. 1-13; Oct. 27-31, 2003.
Osamu Ukimura et. al; "Real-Time Transrectal Ultrasound Guidance During Laparoscopic Radical Prostatectomy: Impact on Surgical Margins"; vol. 175, 1304-1310, Apr. 2006; (Journal of Urology).
Frederic Devernay et. al: "Towards Endoscopic Augmented Reality for Robotically Assisted Minimally Invasive Cardiac Surgery"; Proceedings of Medical Imaging and Augmented Reality p. 16-20; 2001.
Henry Fuchs et. al; "Augmented Reality Visualization for Laparoscopic Surgery", Proceedings of Medical Image Computing and Computer Assisted Interventions (MICCAI) p. 934-943, 1998.
L. Soler et. al; "Virtual Reality and Augmented Reality in Digestive Surgery"; Third IEEE and ACM International Symposium on Mixed and Augmented Reality (ISMAR 2004) p. 278-279; 2004.
M. Baumhauer et al.; "Soft Tissue Navigation for Laparoscopic Prostatectomy: Evaluation of Camera Pose Estimation for Enhanced Visualization"; In Kevin R. Cleary, Michael I. Miga (Eds.). Proc. SPIE Medical Imaging; 2007: Visualization and Image-Guided Procedures; vol. 6509; Artnr.: 650911; 2007.
M. Baumhauer et al.; Entwicklung Eines Navigationssystems Fuer Die Laparoskopische Prostatektomie. In Handles H, Erhardt J, Horsch A, Meinzer H-P, Tolxdorff T (HRSG.) Informatik Aktuell Bildverarbeitung Fuer Die Medizin 2006, Springer, Heidelberg, pp. 326-330.

* cited by examiner

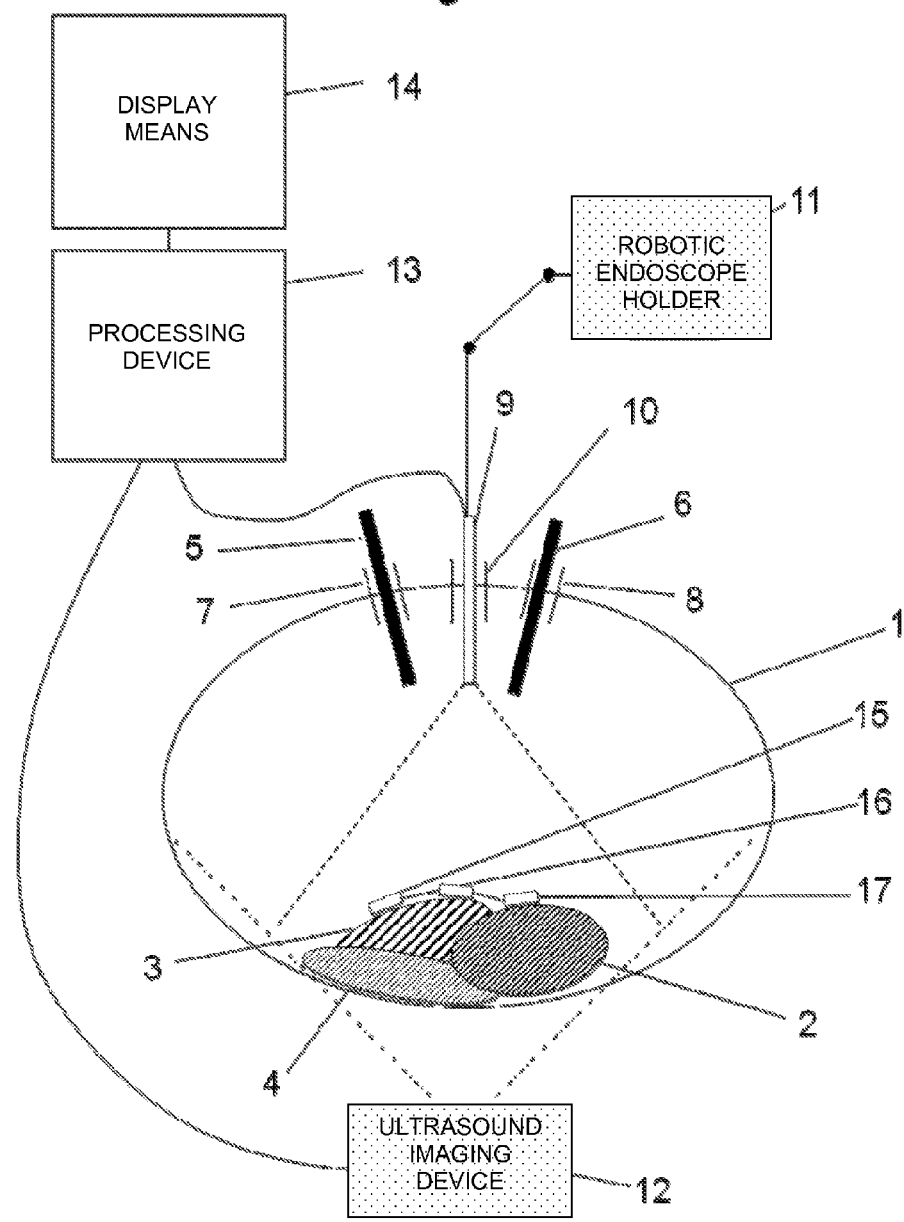

IMAGING SYSTEM FOR FOLLOWING A SURGICAL TOOL IN AN OPERATION FIELD

CROSS REFERENCE TO RELATED APPLICATIONS

This application is a National Phase of PCT/EP2008/060867 filed Aug. 20, 2008, which claims priority to FR 0757158 filed Aug. 24, 2007.

BACKGROUND OF THE INVENTION

1. Field Of the Invention

The present invention relates to the field of medical imaging, more particularly to the monitoring of a surgical instrument in an operative site.

2. State of the Art

Endoscopic surgery requires a high-performance imaging system for visualization of the operative site, to assist the surgeon during surgery.

A certain number of solutions have been developed to improve the viewing offered by the image of a conventional endoscopic camera.

Some systems use images of the operative site acquired before surgery by any system of CT-scan, magnetic resonance imaging, or stereoscopic camera type. Pre-operative images can effectively be used to segment the 3D volume acquired before surgery to isolate the organs of interest, and to relate them with the per-operative imaging system generally consisting of an endoscopic camera. The merging of the 3D images acquired before surgery with the endoscopic images acquired during surgery provide the surgeon with improved visualization of the operative site since the organs of interest are better highlighted. However, existing solutions are relatively cumbersome to implement. In addition, the images using pre-operative data are not fully reliable since there morphological changes may occur between the acquisition of this data and surgery (whether changes with respect to the inter-positioning of the organs and even changes in shape).

Solutions have therefore been developed based solely on the use of data acquired during surgery to overcome these problems.

For example, it has been proposed to use ultrasound images in addition to endoscopic images, so that it is possible to view organs that cannot be seen by the endoscopic camera since they are hidden. For example, the publication titled: "Real-Time Transrectal Ultrasound Guidance During Laparoscopic Radical Prostatectomy: Impact on Surgical Margins" (Journal of Urology, Vol. 175, 1304-1310, April 2006) proposes using an endorectal ultrasound probe operated by a human operator during radical prostatectomy. This allows a significant improvement in the carcinological results of surgery by providing the surgeon with a precise view of the limits of the organ even if such limits are hidden behind the organs visible in the field of vision of the endoscopic camera. The practitioner therefore has at hand an ultrasound image of the operative site to obtain a very clear view of the organs and their relative positioning, and also has an endoscopic image to view the surgical instrument at the operative site.

To facilitate the surgeon's task, it has been proposed to modify the surgical instruments so that they are visible not only in the endoscopic image but also in the ultrasound image. For example, it has been proposed to place ultrasound transducers on the surgical instrument so that it is possible to detect the instrument with the ultrasound imaging device, and optionally permit readjustment between the endoscopic image and the ultrasound image for merging of endoscopic and ultrasound data with a view to obtaining an enhanced image. However, said solution is time-consuming since processing of the data is complex which means that viewing of the enhanced images cannot be made in real time.

Another solution with which to relate and cross-map endoscopic images and ultrasound images is to use an optic locator placed outside the patient so that it can view both the endoscopic camera and the ultrasound probe, then triangulation can be used to readjust the acquired endoscopic and ultrasound images on the basis of the relative position of the external parts of the endoscopic camera and ultrasound probe. However, said solution cannot be implemented under any surgical conditions since it must be possible to visualize both imaging devices. In addition, said system is relatively voluminous which is a major drawback regarding required operating room space.

One purpose of the present invention is to propose an imaging system for the monitoring of a surgical instrument in an operative site inside a cavity of the body of an animal; in particular in a human being, with which it is possible to solve at least one of the above-cited disadvantages.

One purpose of the present invention is in particular to propose a system with which it is possible to visualize enhanced images in close to real time, even in real time.

DISCLOSURE OF THE INVENTION

For this purpose, an imaging system is proposed for the monitoring of at least one surgical instrument in an operative site inside a volume in a body of an animal, in particular a human being, comprising:

at least one endoscopic camera to obtain endoscopic information on the operative site, at least one ultrasound imaging device to obtain ultrasound information on the operative site, a device to process the endoscopic and ultrasound data, characterized in that it further comprises at least three markers intended to be positioned in the operative site, said markers being mobile relative to the instrument, each marker being adapted so that it can be viewed both by the endoscopic camera and by the ultrasound imaging device, so that the endoscopic data can be cross-mapped with the ultrasound data by the processing means.

Other preferred but non-limiting aspects of the imaging system are the following:

the processing device comprises means to merge the endoscopic data and ultrasound data from the cross-mapping thereof and to obtain a representation of the operative site from the merged data;

the system further comprises a device to display the representation of the operative site from the merged data;

the markers are formed of a biocompatible substance comprising a dye so that the marker can be recognized by the endoscopic camera;

the markers are formed of a biocompatible substance containing fluorophore particles emitting a signal enabling the marker to be recognized by the endoscopic camera;

the markers are formed of a biocompatible substance containing a contrast product recognized by the ultrasound imaging device;

the substance forming the markers has sufficient cohesion to prevent said substance from separating, this substance being in the form of a liquid or paste;

the markers contain an envelope formed in a biocompatible material transparent to ultrasound;

the markers comprise an energy source;

the markers comprise a device to emit a light signal recognized by the endoscopic camera, said emitting device being powered by the energy source;

the markers comprise a device emitting an ultrasound signal recognized by the ultrasound imaging device, said emitting device being powered by the energy source;

the device emitting an ultrasound signal comprises at least one piezoelectric transducer;

the device emitting an ultrasound signal comprises at least one capacitive micro-machined ultrasonic transducer (CMUT);

the device to receive an ultrasound signal may comprise at least one piezoelectric transducer;

the device to receive an ultrasound signal may comprise at least one capacitive micro-machined ultrasonic transducer (CMUT);

the markers have a cavity filled with a fluid containing a contrast product recognized by the ultrasound imaging device;

the markers comprise one portion coated with a biocompatible retroreflective material recognized by the endoscopic camera;

the markers comprise one portion coated with a biocompatible paint recognized by the endoscopic camera;

the paint contains fluorophore particles, said fluorophore particles emitting a signal recognized by the endoscopic camera;

the markers comprise attachment means so that they can adhere inside the volume at the operative site;

the markers are fixed relative to each other;

the markers are connected together by a structure to prevent movement of the markers relative to each other;

the ultrasound imaging device consists of a probe intended to be inserted in the body of the animal;

the system comprises at least one robot able to carry at least one imaging means from among the endoscopic camera and the ultrasound imaging device, the robot permitting controlled movement of said imaging means.

BRIEF DESCRIPTION OF THE FIGURES

Other characteristics and advantages will be further apparent from the following description given solely for illustration purposes and is non-limiting, which is to be read with reference to the appended figures amongst which:

FIG. 1 is a schematic illustration of the imaging system to monitor a surgical instruction in an operative site located inside a cavity of a patient;

DETAILED DESCRIPTION OF THE INVENTION

Figure 2A:
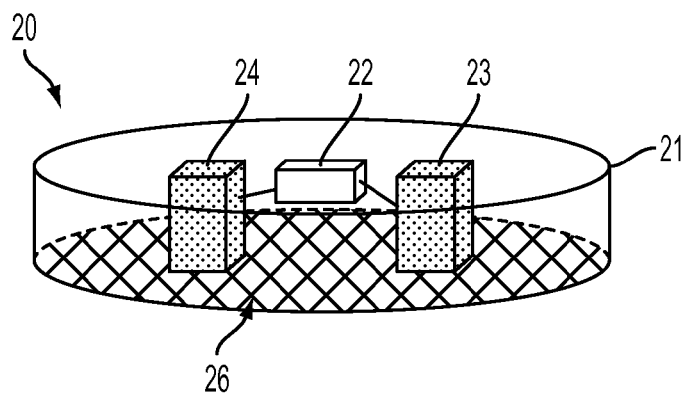
FIG. 2A is a schematic illustration of one embodiment of a marker used in the imaging system in FIG. 1.

FIG. 1 schematically illustrates the imaging system for the monitoring of surgical instruments in an operative site inside a volume 1 of the body of a patient under endoscopic surgery. This volume 1, or volumetric region, forms a cavity 1, this cavity being natural or artificial created in this case by injection of air into the volume.

As schematically depicted in FIG. 1, one or more incisions are made in the cavity 1, these incisions being used to insert surgical instruments (5, 6). These incisions are made using trocars (7, 8) which are inserted through the wall forming the cavity 1 and which are used as portals for the instruments to be inserted inside the cavity 1.

During endoscopic surgery, it is essential for the surgeon to have a proper view of the instruments (5, 6) in relation to the organs (2, 3, 4) present in the operative site.

For this purpose, the imaging system comprises firstly conventional photosensitive imaging means inserted in the cavity 1 via endoscopic route. Conventionally, one or more endoscopic cameras are used, adapted for viewing of the operative site. These endoscopic cameras allow video or photographic images of the operative site to be obtained, which more generally are called endoscopic images.

In FIG. 1, only one endoscopic camera 9 is shown, but it is recalled that a plurality of cameras may be used, notably if it is desired to obtain three-dimensional information (3D) on the operative site. Endoscopic cameras can effectively form stereoscopic sensors by means of which 3D images of the operative site can be reconstructed.

The endoscopic camera 9 is inserted into the cavity 1 via a trocar 10 which may or may not be dedicated to the endoscopic imaging means.

The endoscopic camera 9 can be handled directly by the surgeon, or by an assistant whose task is solely to guide the endoscopic imaging means so that the surgeon can focus on the surgery to be performed.

A robotic endoscope holder 11 can also be used which is provided to perform controlled guiding of the endoscopic camera 9 inside the cavity. The robotic endoscope holder 11 is more precisely capable of tracking the instruments in automated fashion, by image processing for example. This allows the surgeon to concentrate solely on the surgical task since no orders need to be given to an assistant, the robotic endoscope holder being self-operative for movement of the endoscopic camera.

Preferably, the robotic endoscope holder is of small size so that it can be positioned relatively close to the patient, without hampering the surgeon. For example, a robotic endoscope manipulator of VikY type can be used marketed by Endocontrol. For a more detailed description of this device, it is helpful to refer to the publication by P. Berkelman, P. Cinquin, E. Boidard, J. Troccaz, C. Létoublon, et al titled "Development and testing of a compact endoscope manipulator for minimally invasive surgery" (Journal of Computer Aided Surgery, 2005. 10(1): p. 1-13).

It is also useful to use ultrasound imaging means allowing ultrasound images of the operative site to be obtained, which will provide the surgeon with additional information during surgery, particularly with a view to obtaining a more precise view of the organs (2, 3, 4). These ultrasound imaging means in particular allow the visualisation of organs 4 which are not at all visible or can only be seen in part by the endoscopic imaging device 3, 4. In particular, ultrasound imaging in Doppler mode can easily identify vascular structures. It may be of particular advantage for example in radical prostatectomy, for locating of the "neuro-vascular bundles", which must be spared and which the surgeon often has difficulty in identifying in endoscopic images alone.

Here again, several ultrasound imaging devices can be used, even if only one ultrasound imaging device 12 is shown in FIG. 1.

This ultrasound imaging device 1 can be placed outside the patient. It may also consist of an ultrasonic probe placed for example in an organ of the patient that is accessible via natural routes (rectum, bladder, urethra, etc.) or by puncture (vessel, joint space, of the knee for example, etc.). For radical prostatectomy, this ultrasound imaging device 12 may therefore be positioned in the rectum of the patient. Another solution is to place it directly in the cavity 1 via endoscopic route.

As for the endoscopic camera 9, the ultrasound imaging device 12 can be carried by a robot to hold it in position and to control any change in position.

By using a robotic endoscope holder of small size, such as the above-mentioned VikY system developed by Endocontrol, it is possible to position the device at points that are generally non-accessible, without however causing any hindrance to the surgeon. In addition, the space taken up by the imaging means is reduced, which is of particular advantage.

The different imaging device, namely the endoscopic camera or cameras 9, the ultrasound imaging device(s) 12 are coupled with a processing device 13 capable of processing the different data received i.e. both endoscopic data and ultrasound data.

This processing device 13 comprises computing means to synthesize the different data received for a synthesized, enhanced image of the operative site, this image being displayed on any display means 14. The image is said to be enhanced since it integrates both endoscopic data and ultrasound data, so as improve visualization of the instruments (5, 6), and organs (2, 3, 4) at the operative site and facilitate surgery under endoscopy.

However, in order to be able to synthesize this enhanced image, the processing means 13 require additional information allowing cross-mapping of the endoscopic data with the ultrasound data.

For this cross-mapping, it is proposed to use means to create a reference system common to the endoscopic and ultrasound images, in order to relate these images with each other and hence the corresponding data.

For this purpose markers are used, these markers being adapted so that they can be seen both by the endoscopic camera 9 and by the ultrasound imaging device 12.

More precisely, a minimum number of three markers (15, 16, 17) is used so that it is possible to triangulate precisely and to obtain three-dimensional positioning of the endoscopic and ultrasound data.

Since these markers (15, 16, 17) can be seen both in the endoscopic images and in the ultrasound images, they can be used as references for relating the different data. The computing means of the processing means 13 use these common data as basis to merge the endoscopic and ultrasound data in order to synthesize the desired enhanced image.

The markers (15, 16, 17) are adapted so that they can be inserted in the cavity 1, at the operative site, preferably via one of the trocars (7, 8), 10. The markers are therefore adapted so that they can be inserted into the cavity of the operative site via endoscopic route without necessarily having to be rigidly attached to the patient.

They are then positioned by the surgeon in the operative site so that they lie in the field of observation of the endoscopic camera 9 and of the ultrasound imaging device 12. They may for example be placed on or attached to some organs in the region of interest of the operative site. It is to be noted that the closer the markers lie to the organs of interest, the better they are visible in the ultrasound images. This makes it possible to use a three-dimensional ultrasound imaging device 12 whose field of "vision" is often restricted, or to minimize the movements required if the ultrasound imaging device 12 is two-dimensional.

This cross-mapping solution is very simple; in particular it requires very little computing which is quickly carried out. Also, the invention enables the operator to view the position of the instruments in close to real-time, even in real time, with respect to organs that are solely visible by ultrasound since the only computing performed concerns image readjustment.

This is particularly advantageous compared with known methods which allow direct instrument monitoring by placing specific monitoring devices on the instrument, such as specific markers which can be observed by an ultrasound imaging device.

Figure 2B:
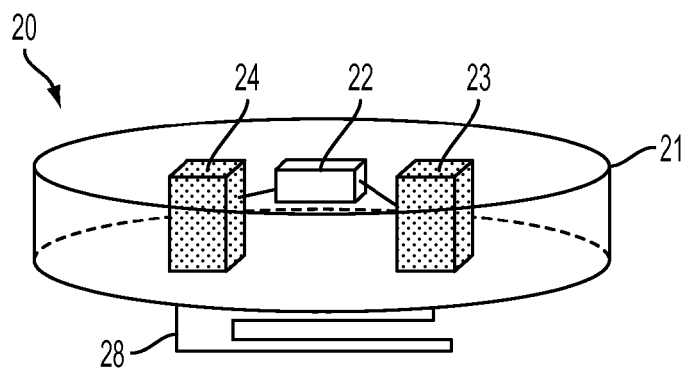
FIG. 2B is a schematic illustration of another embodiment of a marker used in the imaging system in FIG. 1.
Figure 3:
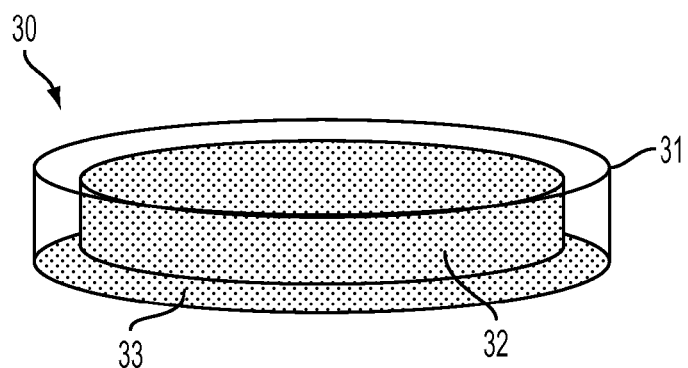
FIG. 3 is a schematic illustration of another embodiment of a marker used in the imaging system shown in FIG. 1.

The markers (15, 16, 17) may be of any shape, the only important aspect being that they are able to be inserted into the cavity 1 via the trocars or using a needle. They may for example be in the shape of small cylindrical pellets as illustrated in FIGS. 2 and 3. Such pellets preferably have a diameter and height of less than 5 mm. For radical prostatectomy, markers may alternatively be used which consist of a needle of which one end comprises at least one capacitive micromachined ultrasonic transducer (CMUT). The very small size of these transducers means that they can be integrated directly in a needle. Each needle is inserted via endoscopic route through the tissues which mask the prostate for the endoscopic camera, until the CMUT transducer comes into contact with the prostate, and so that a sufficient part of the needle can be seen by the endoscopic camera.

It is not necessary for the markers (15, 16, 17) to be connected together. All that is very important is that these markers (15, 16, 17) should be fixed during each image acquisition by the imaging devices, which is assumed to be possible since the acquisition times are very short. The markers can therefore be mobile relative to each other provided that they can be seen by the two imaging systems simultaneously or almost simultaneously i.e. at time intervals that are sufficiently short so that their relative movements are negligible. At all events, this may be imposed by time synchronization of the acquisitions by the imaging devices. The use of separate markers, hence mobile relative to one another, allows easier insertion of the markers (15, 16, 17) into the cavity 1.

The advantage of using said markers, which can act as reference system common to the two imaging systems, is that it is possible to perform quick computing to estimate geometric transformations between the reference system for the endoscopic images and the reference system for the ultrasound images, which is even more advantageous if the endoscopic and ultrasound data are obtained simultaneously.

For the computing time of readjustment between each acquisition to be even more rapid, it is possible to connect the markers (15, 16, 17) using connection means of greater or lesser flexibility. This embodiment is shown in FIG. 1. Therefore, the movements of the markers relative to each other are reduced so that readjustment is simpler. A flexible connection also avoids complicated insertion of the markers (15, 16, 17) into the cavity 1 since the assembly thus formed can be deformed relatively easily.

To avoid any readjustment between acquisitions, it is also possible to connect the markers (15, 16, 17) rigidly via articulations which allow their insertion into the cavity 1 via trocars whilst ensuring sufficient rigidity after deployment.

As indicated above, the markers are adapted so that they can be recognized both by a photosensitive imaging device (such as an endoscopic camera) and an ultrasound imaging device (such as an ultrasonic probe). Several solutions can be envisaged to form said markers.

A first solution which is illustrated in FIG. 2, is to use a marker 20 having an envelope 21 enclosing an energy source 22 such as a micro-battery. Therefore the energy source 22 can be used to power the light and/or ultrasound emitting devices. Said marker is said to be an active marker.

A device 23 may effectively be provided which emits radiation that is recognized by the endoscopic camera; it is typically a light source such as a diode for example.

The marker 20 also encloses a device 24 emitting ultrasounds which are recognized by the ultrasound imaging device 12, this ultrasound emitting device 24 being powered by the energy source 22.

The ultrasound emitting device 24 may for example be a piezoelectric transducer capable of emitting ultrasound waves within the detection range of the ultrasound imaging device 12. It is also possible to use a capacitive micro-machined ultrasonic transducer (CMUT) which has the advantage of being very small and can therefore easily be incorporated in a small volume envelope 21.

The envelope 21 is fabricated in a biocompatible material transparent to ultrasound waves and to light waves so that the signals emitted by the light-emitting devices 23 and ultrasound emitting devices 24 can be recognized by the endoscopic 9 and ultrasound 12 devices.

In addition, the marker comprises an attachment system to facilitate attachment in the cavity 1. Provision may be made for example for clip-on means 28 (as shown in FIG. 2B) or biological glue 26 (as shown in FIG. 2A) on the surface of the envelope 21. The envelope 21 may also have a special shape facilitating its adhering to the organs; it may be in the form of a suction pad for example.

FIG. 3 shows a marker 30 according to one possible embodiment. In this case, the marker does not have an integrated energy source, which means that it is a passive marker.

The envelope 31 in this case has a cavity which can be filled with a fluid 32 for example a contrast product recognized by the ultrasound imaging device. Most often, these contrast products are emulsions containing micro air bubbles such as the product Levovist™ marketed by Schering.

Since the envelope 31 is transparent to ultrasound, the contrast product will show up with strong intensity in ultrasound images making it possible precisely to position the markers in the ultrasound image.

One portion of the envelope is coated with a paint or retroreflective material 33 which can increase visibility and contrast of the marker 30 in endoscopic images. A biocompatible paint or retroreflective material 33 is suitably used. The paint or retroreflective material 33 being deposited on the envelope 31, the envelope 31 is no longer necessarily required to be in a light-transparent material.

To further improve visibility and contrast of the marker 30 in the endoscopic images, it is possible to use a paint containing fluorophore particles. It is effectively also possible to provide for a fluorophore-exciting light source, this light source possibly being placed on the endoscopic camera or at any other point. The endoscopic camera is also adapted to recognize the signal emitted by the fluorophores. In addition, the use of fluorophore particles is of particular advantage if the field of vision is obstructed by tissue to the extent that the marker cannot be seen by the endoscopic camera. By using a light source emitting a light signal in the transparency window of biological tissues (i.e. at a wavelength preferably of between 750 nm and 1350 nm), the signal emitted by excitation of the fluorophores can be perceived by the endoscopic camera (adapted to these particular wavelengths) despite hindering by tissues.

It is to be noted that the use of a biocompatible paint could also be envisaged for the marker 20 described previously and illustrated in FIG. 2. This paint could supplement or replace the light-emitting device 23.

Another type of passive marker consists of a biocompatible material intended to be injected directly inside an organ, hence intrinsically bound to this organ. These markers are said to be internal markers, as compared with the previous markers which are rather more intended to be deposited on the surface of or in contact with an organ present in the volume of the operative site, and which can therefore be termed external markers (relative to the organ). Said internal markers may for example be of liquid type or in the form of a biocompatible paste.

Said markers are adapted so as not to diffuse inside the organ after being injected, so that they remain within a particular volume in the form of a cluster for example. Therefore, a liquid marker can be used for example which is injected into specially chosen region of an organ so that it collects i.e. forms a cluster of this particular liquid in the region of the organ. Said markers can also consist of a substance adapted so that it maintains its shape and therefore has strong cohesion so that the material does not separate. A viscous liquid can be used for example i.e. having strong viscosity or a material whose composition can ensure such cohesion such as a gel or paste for example.

Evidently, these markers must be particularized so that they can be seen by the different image acquisition means. For example, with respect to photosensitive detectors, stained sterile water can be used e.g. a universal water-soluble dye of methylene blue type. Another solution consists of using sterile water in which a biocompatible fluorophore is incorporated. In this latter case, fluorophore particles are chosen which can be excited by wavelengths lying inside the "transparency window of biological tissues" (for example between 700 nm and 800 nm) and able to re-emit a signal in this same transparency window. The advantage is then that the "internal marker" can be injected deeper inside the organ whilst remaining visible for conventional cameras or cameras sensitive to the near infrared. These different liquid or "pasty" markers may if necessary be enhanced with biocompatible ultrasound contrast products e.g. of micro-bubble type (this ultrasound contrast product being increasingly used). They provide ultrasound detection sensitivity. A contrast product may for example consist of a product that is fully opaque to ultrasound which means that the markers will be apparent in the ultrasound image.

These markers are then injected into the organ regions by means of a suitable device (needle, iontophoresis device for example) so that it is possible to detect at least three "spots", corresponding to three separate collections of liquid for example.

Particular care is to be given to injection conditions so as to maintain, at least during the cross-mapping phase, a characteristic aspect of each "spot" (e.g. in the form of a collection) at a depth adapted to the detection characteristics of the imaging systems, permitting easy non-ambiguous identification thereof in the different imaging systems.

These internal passive markers can therefore be seen firstly by the photosensitive imaging system owing to the optical properties of the injected material, but also by the ultrasound system subsequent to localized modifications characteristic of acoustic impedances after injection of the marker. By way of schematic illustration, with respect to surface injections into the organ of methylene blue dissolved in sterile water, it will be sought to detect blue "spots" on the surface of the organ using photosensitive imaging and to detect hypo-echogenic collections by ultrasound imaging.

A procedure will now be described which will permit an enhanced image to be obtained to assist the surgeon in handling surgical instruments at the operative site. For reasons of simplicity, this procedure is described with respect to "external" markers or contacts (as opposed to the markers previously identified as "internal").

An endoscopic camera and ultrasonic probe are used. A 3D ultrasonic probe is preferred to allow acquisition of the volume of interest from a single position of the probe, therefore without having to set the probe in movement. It is recalled that the endoscopic camera and ultrasonic probe may be carried by robots to allow improved holding in position and provide the possibility of controlled guiding of the imaging devices. In some cases, this also permits mobilization of the organs, for example using an endorectal or endourethral ultrasound probe for radical prostatectomy.

The markers are then inserted via one of the percutaneous orifices and "released" into the operative site. The surgical instruments are then used to position the markers correctly in the operative site, as close as possible to the region of interest, particularly so that the portion of markers in contact with the organs allows the transmission of ultrasound waves.

Each time an enhanced image is to be synthesized, the following steps are to be carried out.

Firstly, endoscopic and ultrasound images must be simultaneously acquired avoiding movements of the operative site as much as possible.

Then, the acquired ultrasound data is processed to determine the position of the markers. It is possible for example to determine the 3D positions of the markers using a 3D ultrasound imaging device 12 or any other device or method known to the person skilled in the art. The advantage of using active markers with a transducer (piezoelectric or CMUT) is that it permits very simple segmentation which does not require human intervention. On the contrary, for a passive marker, it is preferable, at least at the start, to enter manual data. It is noted however that automatic segmenting from passive markers is possible if one has rough knowledge of the relative positioning of the markers, this rough positioning possibly being known by means of the more or less flexible connections linking the markers together. This step therefore provides n three-dimensional points $U_i$, which are the centres of the transducers or of the contrast product.

Let $C_i$ be the n three-dimensional points corresponding to the centres of the light-emitting devices or of the retroreflective or painted surfaces of the markers, and let $d_i$ be the distances between $U_i$ and $C_i$. The values of $d_i$ are known at the time of fabrication of the markers (15, 16, 17). By observing these markers through the endoscopic camera, n two-dimensional points $B_i$ are obtained by projection of the three-dimensional points $C_i$ in the endoscopic image. Prior intrinsic calibration of the endoscopic camera allows deducing of n straight lines $D_i$.

Cross-mapping of the images consists of identifying the vector p having 6 parameters (3 rotations and 3 translations) of the matrix linking together the reference systems of the endoscopic camera and of the ultrasonic probe. If $e_i$ denotes the distance between the centre $U_i$ and the straight line $D_i$ for each marker, it is found that $e_i$ is equal to or less than $d_i$ when cross-mapping is perfect. Approximation of the cross-mapping parameters can therefore be obtained using the non-linear least square method (e.g. the Levenberg-Marquardt method), by minimizing $\Sigma e_i * e_i$. This approximation will be sufficient if the distances $d_i$ are short, typically in the order of one millimeter (this is particularly the case with markers using CMUT technologies in which the ultrasound transducers are of very small size). If this approximation is insufficient, all that is required is to increase the number of markers or to use an additional endoscopic camera (in this latter case, it becomes possible to obtain points $C_i$ directly).

It is also noted that it may be of advantage, to facilitate cross-mapping, to have a prior estimate of the initial attitude of the reference system related to the endoscopic camera and of the reference system related to the ultrasonic probe, to avoid local minima conventionally encountered with cross-mapping methods. For this purpose, it is possible to differentiate the markers e.g. using different patterns (size, colour, etc.) visible by the endoscopic camera, and different ultrasound characteristics for each marker (size, intensity, frequency, number of sources, etc.).

All that is subsequently required is to merge the data from the two imaging systems to synthesize the enhanced image which will be displayed on the surgeon's monitoring screen. The surgeon is therefore able to see not only the instruments shown by the endoscopic camera, but also the organs which are only visible via ultrasound.

If internal markers are used, the adapted procedure is conducted in similar manner. As an example we shall give consideration to "internal" markers containing fluorophores. These markers are injected into different regions of the organs. Then, for the ultrasound imaging system, the n three-dimensional points $U_i$ are determined that are the centres of the local ultrasound regions with impedance characteristic of the injection regions. It is recalled that these three-dimensional points $U_i$ lie inside the organs.

The injection of "internal" markers is performed as appropriate, in particular in terms of depth so that video-sensitive acquisition of the signal characteristic of the marker is effectively possible (for example, use of a biocompatible fluorophore with an emission wavelength in the near infrared for deep injections). Using the previous denotations, the centres $C_i$ of the three-dimensional points appear as the emitting centres of the injected regions. In this approach, they merge with the points $U_i$. The $C_i$s are observed indirectly by the acquisition system, in the form of points $B_i$, located on the surface of the organ. The prior intrinsic calibration of the endoscopic camera leads to obtaining n straight lines $D_i$ (which are none other than the straight lines $B_i C_i$).

As previously, the cross-mapping of the images consists of identifying the vector p with 6 parameters of the matrix connecting the reference systems of the endoscopic camera and of the ultrasonic probe, by minimizing a quadratic functional $\Sigma e_i * e_i$ in which values $e_i$ respectively represent the distance of points $U_i$ (ultrasound system) to the straight lines $D_i$ (video system).

The reader will appreciate that numerous modifications may be made hereto without materially departing from the novel teachings and advantages described herein. Therefore, any modifications of this type are to be incorporated within the scope of the presented imaging system.

The invention claimed is:

1. An imaging system to monitor at least a surgical instrument in an operative site inside a volume in the body of an animal, said system comprising:
    a first structural imaging modality comprising at least one endoscopic camera to obtain data comprising video or photographic structural images of the operative site, the at least one endoscopic camera detecting visible or near IR radiation to form said video or photographic images of the operative site,
    a second structural imaging modality comprising at least one ultrasound imaging device to obtain ultrasound data on the operative site,
    a processor to process the endoscopic and ultrasound data obtained simultaneously by the endoscopic camera and the ultrasound imaging device respectively, the processor being configured to synthesize an enhanced image of the operative site by merging the ultrasound data with the data from the at least one endoscopic camera,
    wherein the imaging system further comprises at least three markers intended to be positioned in the operative site, said markers being mobile, each marker being adapted to be detected by both the endoscopic camera and the ultrasound imaging device, and said at least three markers forming a common reference system to be adapted by the processor to perform cross-mapping of the endoscopic and ultrasound data obtained simultaneously, wherein each marker includes:
a respective envelope,
a respective light source that emits visible or near IR radiation for detection by the endoscopic camera, and
a respective ultrasound emitter that emits ultrasound for detection by the ultrasound imaging device, the light source and the ultrasound emitter being contained within said envelope.

2. The system of claim 1, further comprising means for time synchronization of the data acquired by the endoscopic camera and the ultrasound imaging device.

3. The system of claim 1, further comprising a display device to display to a user of the surgical instrument the enhanced image of the operative site from the merged data.

4. The system of claim 1, wherein each envelope comprises a biocompatible material transparent to ultrasound.

5. The system of claim 1, wherein each of the markers comprises an energy source.

6. The system of claim 5, wherein the light source in each marker is powered by the respective energy source of the marker.

7. The system of claim 5, wherein each ultrasound emitter emits a signal recognized by the at least one ultrasound imaging device, said ultrasound emitter in each marker being powered by the respective energy source of the marker.

8. The system of claim 7, wherein at least one of the ultrasound emitters comprises at least one piezoelectric transducer.

9. The system of claim 7, wherein at least one of the markers comprises a needle, and the ultrasound emitter of said at least one of the markers comprises at least one capacitive micro-machined ultrasonic transducer (CMUT) integrated in the needle.

10. The system of claim 1, wherein at least one of the markers comprises an attachment system for adhering inside the volume of the operative site.

11. The system of claim 1, wherein the markers are connected together to avoid movement of the markers relative to one another.

12. The system of claim 1, wherein the markers are fixed relative to one another.

13. The system of claim 1, wherein the ultrasound imaging device comprises a probe intended to be inserted into the body of the animal.

14. The system of claim 1, comprising a robotic manipulator that holds and permits controlled movement of at least one of the endoscopic camera and the ultrasound imaging device.

15. The system of claim 1, wherein:
each marker is a self-contained unit constructed for independent positioning within the operative site and for attachment to an organ in the body and/or to other markers,
the envelope being transparent to the radiation detected by the endoscopic camera and to ultrasound detected by the ultrasound imaging device,
at least one of the markers having a pattern or emission characteristic with respect to radiation detected by the endoscopic camera or to ultrasound detected by the ultrasound imaging device different from at least another of the markers.

16. An imaging system to monitor at least a surgical instrument in an operative site inside a volume in the body of an animal, said system comprising:
a first structural imaging modality comprising at least one endoscopic camera to obtain data comprising video or photographic structural images of the operative site, the at least one endoscopic camera detecting visible or near IR radiation to form said video or photographic images of the operative site,
a second structural imaging modality comprising at least one ultrasound imaging device to obtain ultrasound data on the operative site,
a processor to process the endoscopic and ultrasound data obtained simultaneously by the endoscopic camera and the ultrasound imaging device respectively, the processor being configured to synthesize an enhanced image of the operative site by merging the ultrasound data with the data from the at least one endoscopic camera,
wherein the imaging system further comprises at least three markers intended to be positioned in the operative site, said markers being mobile,
each marker being adapted to be detected by both the endoscopic camera and the ultrasound imaging device, and
said at least three markers forming a common reference system to be adapted by the processor to perform cross-mapping of the endoscopic and ultrasound data obtained, simultaneously,
wherein:
each marker is sized and shaped so as to be introduced into the operative site via one or more trocars,
at least one of the markers is coated with a paint or retroreflective material that increases visibility or contrast of the at least one of the markers in the endoscopic video or photographic images, and
the processor is configured to synthesize the enhanced image of the operative site such that one or more features of the operative site that are not visible in the endoscopic video or photographic images are shown in the enhanced image.

17. The system of claim 16, wherein at least one of the markers comprise a biocompatible substance comprising a dye that emits radiation detected by the endoscopic camera.

18. The system of claim 17, wherein the substance of at least one of the markers has sufficient cohesion to prevent said substance from separating.

19. The system of claim 16, wherein at least one of the markers comprise a biocompatible substance comprising fluorophore particles that emits radiation detected by the endoscopic camera.

20. The system of claim 16, wherein the markers comprise a biocompatible substance comprising a contrast product recognized by the ultrasound imaging device.

21. The system of claim 16, wherein at least one of the markers has a cavity filled with a fluid comprising a contrast product recognized by the ultrasound imaging device.

22. The system of claim 16, wherein at least one of the markers comprises a portion coated with a biocompatible retroreflective material recognized by the endoscopic camera.

23. The system of claim 16, wherein at least one of the markers comprises a portion coated with a biocompatible paint recognized by the endoscopic camera.

24. The system of claim 23, wherein the biocompatible paint comprises fluorophore particles, said fluorophore particles emitting radiation detected by the endoscopic camera.

25. The system of claim 16, wherein at least one of said markers comprises an ultrasound emitter.

\* \* \* \* \*